United States Patent [19]

Reinhard et al.

[11] Patent Number: 5,030,087
[45] Date of Patent: Jul. 9, 1991

[54] DEVICE FOR SUPPLYING LIGATURE WIRES IN CONJUNCTION WITH A PACK OF LIGATURE WIRES

[76] Inventors: Peter Reinhard, Winzerstrasse 6, 8953 Dietikon, Switzerland; Ulrich Hübers, Hauptstrasse 5, 7600 Offenburg, Fed. Rep. of Germany

[21] Appl. No.: 521,684

[22] Filed: May 10, 1990

[30] Foreign Application Priority Data

May 10, 1989 [CH] Switzerland .................. 1760/89

[51] Int. Cl.⁵ .............................................. A61C 3/00
[52] U.S. Cl. ........................................ 433/3; 433/15
[58] Field of Search ................ 433/2, 3, 15; 606/144, 606/148; 140/93 A, 118; 206/339, 63.3, 63.5

[56] References Cited

U.S. PATENT DOCUMENTS 3,596,357 8/1971 Matsumoto .......................... 433/3
4,875,855 10/1989 Beckett ................................ 433/3

Primary Examiner—Cary E. Stone

[57] ABSTRACT

A device for supplying individual ligature wires inserted as a pack of wires in a casing of the device has an operating arm. A pack of ligature wires is inserted into a recess provided in the casing. Pressure is exerted onto the pack of wires by a push rod. In each case the lowermost ligature wire in the pack is pressed into a recess formed in the bottom of the casing. Then the wire from this readiness position is advanced into a transfer position by a driving pawl mounted in a slide. The movement is carried out by pressing the operating arm, the free end of which projects into a slot of the slide and, on pressing the operating arm, advances the slide and therefore the ligature wire into the transfer position. In the transfer position, the end portions of the ligature wire can be grasped by a tool, e.g. a twister and removed from the casing to be placed into the area of use.

19 Claims, 3 Drawing Sheets

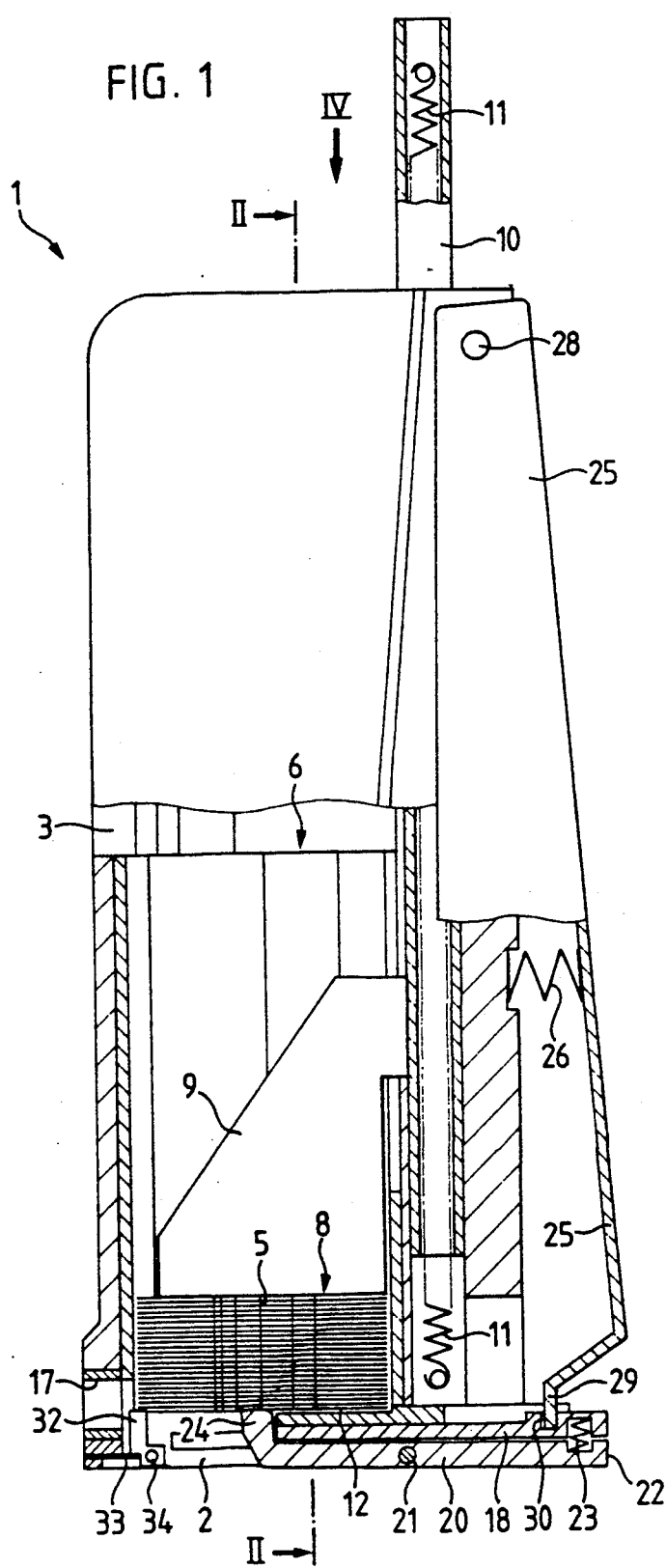
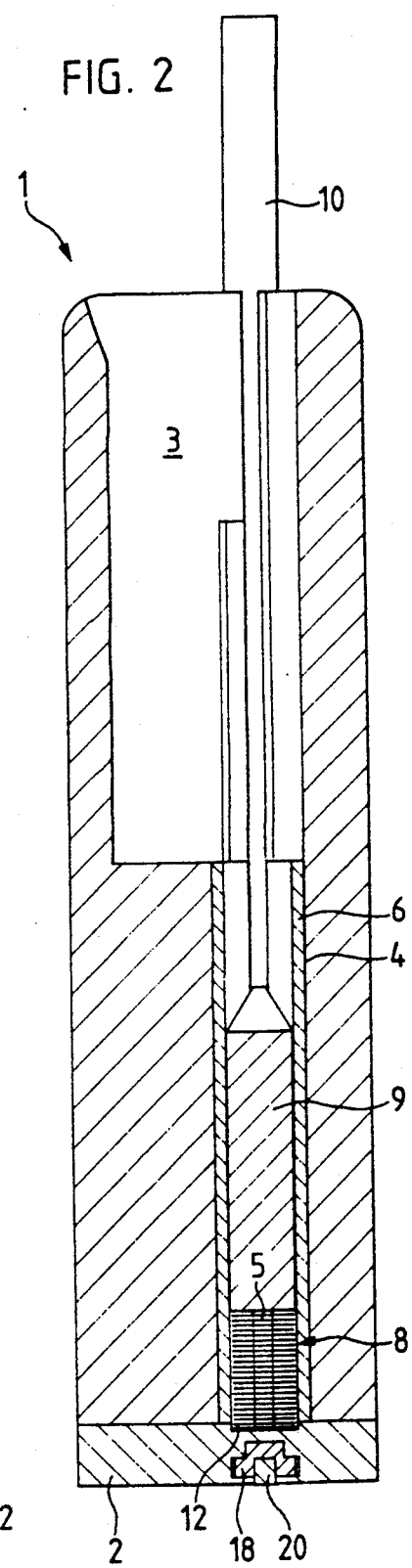

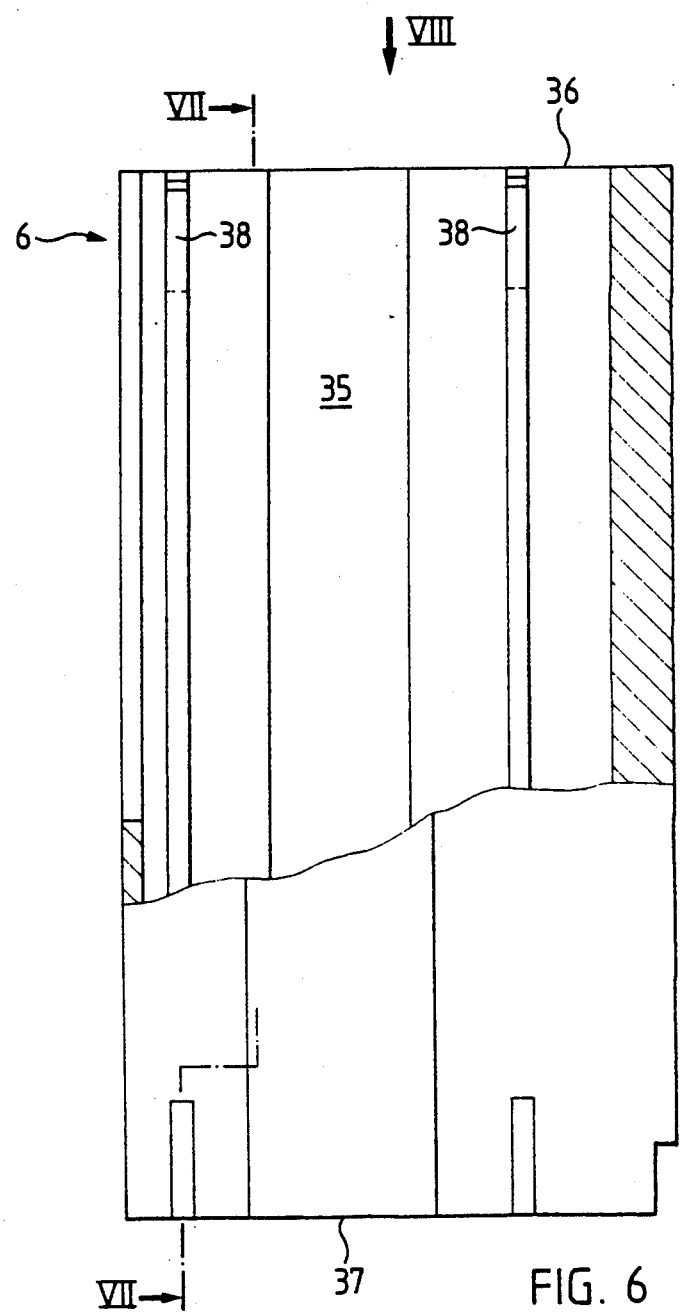
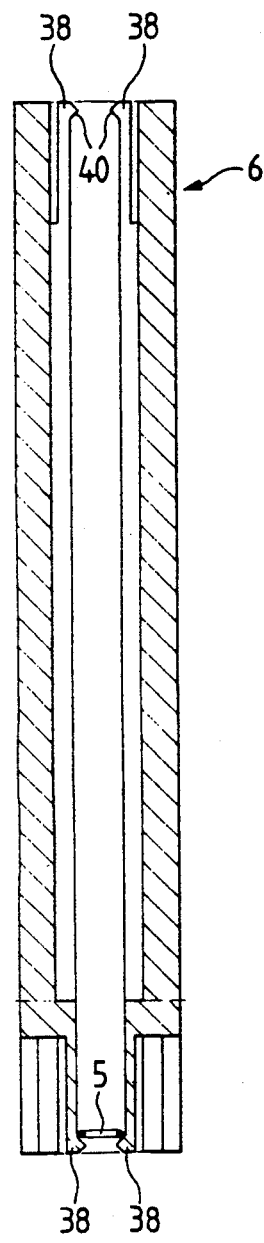
FIG. 6
FIG. 7
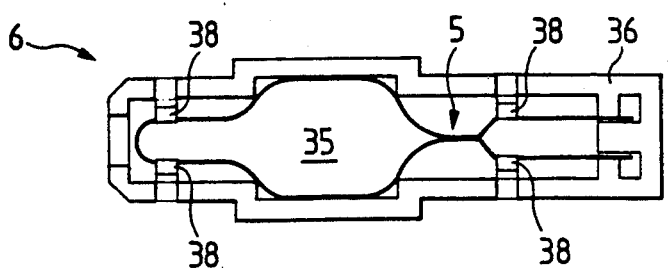
FIG. 8

DEVICE FOR SUPPLYING LIGATURE WIRES IN CONJUNCTION WITH A PACK OF LIGATURE WIRES

BACKGROUND OF THE INVENTION

The present invention relates to a device for delivering individual ligature wires from a pack of such wires for orthodontics, in which device the ligature wires are inserted in a delivery casing.

The field of orthopedics essentially covers the correction of tooth position and jaw abnormalities. A so-called band-clip apparatus is known, which is used for this purpose. The apparatus makes it possible to correct malpositioned teeth. Brackets are fixed to the labial or lingual surface of the teeth, from which brackets is recessed a locking means for the insertion of a wire clip. In order that the force of the slip be transferred to the teeth, it is necessary to fix the clip to the brackets. This fixing can inter alia also be obtained by fine wires, this procedure being called ligature. The application and fixing of such a wire clip is relatively complicated, particularly if it is necessary to correct both the teeth of the upper and the lower jaw.

For ligatures use is made of very fine wires with a thickness of a few tenths of a millimeter, e.g. 0.2 to 0.3 mm. The wires are placed around the brackets and their ends are twisted for fixing the clip in the lock of a bracket. The ligature wire is placed over the clip and extends below two wings arranged on the brackets and from which it cannot be stripped off. Auxiliary means are used to facilitate the twisting of the ligature wires.

A known device called a twister of the present applicant (Swiss patent application 1894/88 of 19.5.88) makes it possible to twist ligature wires much faster. The device has a rod-like construction and a grip for gripping a ligature wire. The grip is connected to a torsion bar arranged within the rod-like device. Threads are formed on the outer circumference of the torsion bar and these cooperate with the threads of the rod. As a result of an axial movement of the rod, a rotary movement is imparted to the torsion bar and therefore to the grip, through which the ends of the ligature wire are twisted for fixing a clip guided in the brackets so that the clip permits the transfer of its force to the teeth. Although the twisting of the ligature wires is accelerated by the twister, it is not possible to overlook the fact that the insertion of the ligature wire into the twister is difficult and time-consuming. The loop-shaped ligature wires are delivered in boxes resting in random manner on one another. It constitutes a very time-consuming process to remove a single ligature wire from a plurality of such wires which are in part hung up on one another.

SUMMARY OF THE INVENTION

It is an object of the present invention not only to supply individual ligature wires in a well-ordered arrangement, but to also provide them in individual form in such a way that the ligature wire can easily be grasped by a twister or a corresponding tool, e.g. surgical needle holders and, immediately following this, can be used for fixing a clip.

According to the invention this and other objects are attained by the device, where the ligature wires are preshaped to form a wire loop with two legs or prongs and are placed individually on top of one another in a delivery casing, the legs of the ligature wires being juxtaposed and horizontal at the same level. As a result, the individual ligature wires rest tightly on one another and always have the same spacing from one another.

Appropriately, the legs of the ligature wires are firmly interconnected in their end portions, e.g. by welding, soldering or gluing. As a result of the firm connection of the two legs the transportation of the individual ligature wire to its transfer position is facilitated.

The invention is described in greater detail hereinafter relative to an embodiment and the attached drawings.

BRIEF DESCRIPTION OF THE DRAWINGS

FIG. 1 is a diagrammatically represented side view, partly in section, of a device for delivering a single ligature wire from a pack, which is brought into a position where it an be grasped by a twister or a similar tool;

FIG. 2 is a section through the device according to FIG. 1 taken along line II—II;

FIG. 6 is a diagrammatically represented side view, partly in section, of a ligature sleeve for receiving a pack of ligature wires which rest individually on one another and are prevented from dropping out by flexible holders;

FIG. 7 is a section of the ligature sleeve according to FIG. 6 taken along line VII—VII; and FIG. 8 is a view of the ligature sleeve according to FIG. 6 taken from direction of arrow VIII of FIG. 6.

DETAILED DESCRIPTION OF THE PREFERRED EMBODIMENTS

Figure 3:
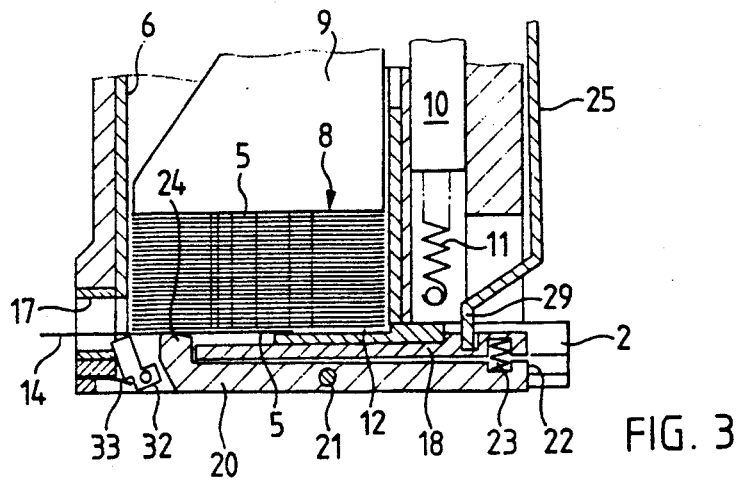
FIG. 3 is a detail of the bottom part of the device shown in FIG. 1 in which an individual ligature wire is in the delivery position.

The present invention is based on the idea that the time taken for fixing a wire clip in orthodontics can in particular be reduced if it is possible to make available the ligature wires such that in each case a single ligature wire is delivered or supplied and grasped by a twister or a similar tool and immediately thereafter can be used for fixing a wire clip. FIGS. 1 to 4 show such a device, which receives a pack of individual ligature wires resting on one another and which in each case delivers a single ligature wire for grasping by a twister. The device shown in FIGS. 1 to 4 has a substantially parallelepipedic delivery casing 1, which is terminated at the underside with a casing bottom 2. The delivery casing 1 has an upwardly open opening 3, which at the bottom merges into a relatively narrow recess or gap 4 (FIG. 2), in which can be inserted a pack 8 of ligature wires 5, cf. FIG. 5. The ligature wires 5 rest on one another in a column-like pack. For this purpose, use is made of a sleeve 6 for receiving the pack of wires in the device of FIGS. 1 to 4 and which holds the wires together as pack 8 of the individual ligature wires resting one on top of another. A push rod 9 presses onto the top of pack 8. The push rod 9 is connected to a guide tube 10 mounted in the delivery casing 1. Within the guide tube 10 is housed a tension spring 11, which is fixed to the delivery casing 1 in the vicinity of its bottom 2 (FIG. 1) and presses the push rod 9 onto pack 8. The push rod 9 has a cross-section similar to that of the ligature wire 5, so that it can be introduced into the sleeve 6.

It is also possible to combine the ligature wires 5 as pack 8 without the ligature sleeve 6, e.g. in that the individual ligature wires would be glued to one another. The ligature wires 5 must then be so firmly held together that they do not drop apart prior to use, whilst the connection between the individual wires 5 must not be too strong so that, on delivering a single ligature wire a deformation occurs to the thin wires, the diameter of which is 0.2 to 0.3 mm. However, if the ligature wires 5 are inserted in the sleeve 6, there is no need for a temporary mutual connection between the ligature wires.

In the casing bottom 2, at the end of gap or recess 4 there is provided a recess 12, the depth of which corresponds to the thickness of individual ligature wire 5. The ligature wire 5 positioned in the recess 12 is in its readiness position, from which it can be moved into a transfer position, cf. FIG. 3, in which an end portion 14 of each of the wires 5 extends through a centering sleeve 17 inserted in the delivery casing 1. In this transfer position, the end portion 14 of the wire 5 can be grasped by a twister and the ligature wire 5 can be directly used for fixing a clip.

A slide 18 is mounted in the casing bottom 2. A driving pawl 20 mounted in slide 18 is pivotably mounted about a pivot pin 21, cf. FIG. 3. Rear end 22 of the driving pawl 20 is subject to the action of a compression spring 23 by which an upwardly bent portion 24 at the front end of the pawl 20 is pressed into the recess 12 formed in the casing bottom 2. By means of the end portion 24, the ligature wire 5 can be moved out of the readiness position into the transfer position shown in FIG. 3, if an operating arm 25 (FIGS. 1 and 3) pivotably mounted on the delivery casing 1 is pressed. At the upper end of the delivery casing 1, the operating arm 25 has a pivot pin 28, whilst its downwardly projecting, free end portion 29 projects into a slot 30 formed in slide 18. If the operating arm 25 is pressed, the slide 18 is moved in the direction of the centering sleeve 17, so that the lowermost single ligature wire 5 positioned in recess 12 is transferred by end portion 4 of driving pawl 20 into the transfer position shown in FIG. 3 as described hereinabove.

A pivotable flap 32 is located in the bottom casing in the vicinity of centering ring 17 for guiding the ligature wire 5. Flap 32 is under the action of a leaf spring 33 and is pivotable about a horizontal pivot pin 34.

FIGS. 6 and 7 show the ligature wire pack-receiving sleeve 6 in detail. Sleeve 6 has a passage 35, in which is inserted pack 8 of ligature wires 5. In order that the ligature wires cannot drop out of the sleeve 6, at the upper and lower ends 36, 37 of sleeve 6, there are provided holding or retaining arms 38, cf. particularly FIG. 7. The holding arms 38 have each a cam-shaped end portion 40 and are also resiliently constructed, so that the ligature wires can be easily introduced into the sleeve 6 due to the expansion of holding arms 38 and, under the action of push rod 9, be forced out of the passage 35. FIG. 7 shows the lowermost ligature wire 5 at the lower end face 37, whilst the whole pack is not shown.

Figure 4:
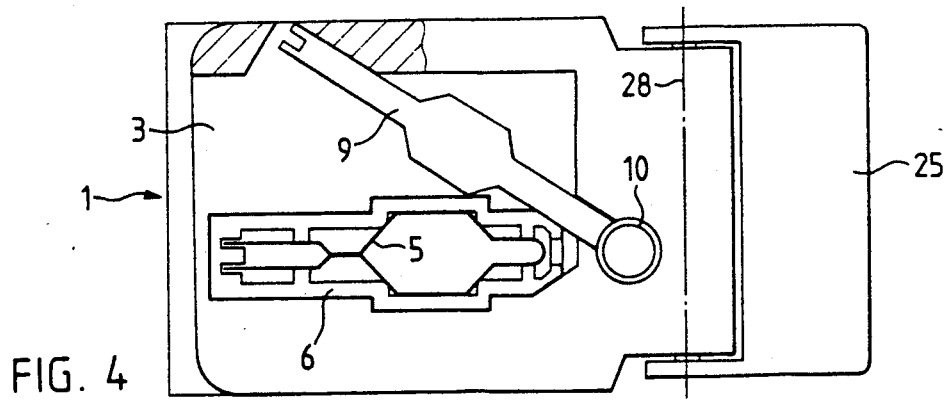
FIG. 4 is a view of the device according to FIG. 1 from direction of arrow IV of FIG. 1, and shown partly in section.
Figure 5:
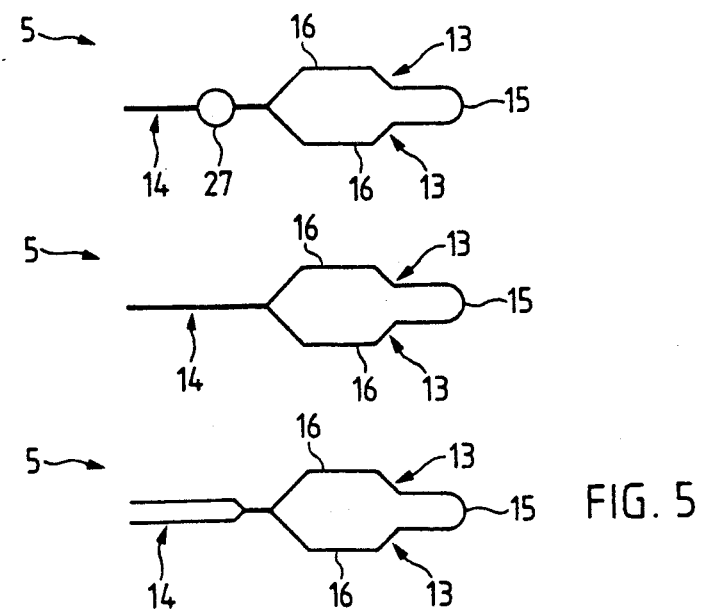
FIGS. 5A–5C illustrate three examples of preshaped ligature wires, the legs of which are interconnected in their end regions.

FIG. 8 shows sleeve 6 in cross-section. The shape of the passage 35 is adapted to the shape of the ligature wire 5, and the gap or recess 4 is profiled accordingly. FIG. 4 shows that the push rod 9 can be swung out laterally in the vicinity of opening 3, so that an empty sleeve 6 can be removed and replaced with a full one. FIG. 4 also shows that the operating arm 25 embraces the delivery casing 1. As shown in FIG. 1, a spring 26 is provided, which ensures that the slide 18 is returned to its starting position, so that the second lowermost ligature wire can be forced by push rod 9 into recess 12 in casing bottom 2.

FIGS. 5A to 5C shows three different shapes of ligature wires 5, which have two legs or prongs 13, and the central parts 16 of which are interconnected by a web 15. It is important that the end portions 14 of legs 13 are at least so partly interconnected so that they are juxtaposed and do not overlap. In the case of FIG. 5A, the end portions 14 of the wire are completely interconnected, with the exception of a small opening 27. The ligature wire 5 of FIG. 5B has completely interconnected end portions 14, whilst the end portions 14 of the ligature wire of FIG. 5C are only interconnected at the transition to the central portion 16 Central portion 16 is shaped in such a way that it can be easily engaged on the brackets.

As a result of the above described device for the delivery of individual ligature wires 5, there is a considerable increase in the speed of loading a twister or other ligating devices (needle holders) with ligatures in orthodontics. This is helped by the fact that the individual ligature wires 5 are made available in packs 8 and can be individually delivered by the aforedescribed device.

There has been disclosed heretofore the best embodiment of the invention presently contemplated. However, it is to be understood that various changes and modifications may be made thereto without departing from the spirit of the invention.

What is claimed is:

1. A combination of a device for supplying ligature wires for orthodontics with a pack of ligature wires, the combination comprising a casing receiving a pack of ligature wires, said ligature wires in the pack being preshaped as wire loops having two legs and being individually placed so as to rest horizontally one on another in said pack inserted in said casing, said legs of each of ligature wires being horizontally juxtaposed at the same level.

2. The combination according to claim 1, wherein end portions of said legs of the ligature wires in said pack are firmly interconnected.

3. The combination according to claim 2, wherein said end portions are interconnected by welding.

4. The combination according to claim 2, wherein said end portions are interconnected by soldering.

5. The combination according to claim 2, wherein said end portions are interconnected by gluing.

6. The combination according to claim 2, wherein said end portions of said legs of the ligature wires are firmly interconnected only over part of the length thereof.

7. The combination according to claim 1, further comprising a sleeve positioned in said casing, said ligature wires being individually stacked one upon another in said sleeve.

8. The combination according to claim 7, wherein said sleeve has end faces provided with resiliently constructed holding means which prevent said ligature wires from falling out from said sleeve.

9. The combination according to claim 8, wherein said holding means include holding arms opposing each other and provided with cam portions.

10. The combination according to claim 1, wherein said device includes access means through which said wires of said pack are individually removable from said casing, said casing including a bottom portion in which a lowermost ligature wire in said pack is in a readiness position, and further comprising means for moving the lowermost wire from the readiness position to a transfer position in which the ligature wire is to be grasped by a tool.

11. The combination according to claim 10, wherein said tool is a twister.

12. The combination according to claim 10, wherein said bottom portion of said casing is formed with a recess having a depth corresponding to a thickness of the individual ligature wire.

13. The combination according to claim 12, wherein said moving means includes a slide positioned in a bottom of said casing, said slide being displaceably guided, and a driving pawl pivotably mounted in said slide and having a bent end portion adapted to project into said recess to drive the lowermost ligature wire and into a central part of the ligature wire positioned in the readiness position.

14. The combination according to claim 13, further comprising an operating arm mounted on said casing and having a free end portion projecting into a rear part of said slide to displace said slide for moving the lowermost ligature wire into the transfer position.

15. The combination according to claim 13; and further comprising a guide flap positioned in front of said slide, said end portions of said legs of the lowermost ligature wire in said pack being guided in said guide flap.

16. The combination according to claim 15, wherein said guide flap is under action of a spring and is pivotably mounted to said casing.

17. The combination according to claim 10, further comprising a sleeve rod acting on said pack inserted in said casing, said push rod being under tension of a spring and pressing said pack against the bottom of said casing.

18. The combination according to claim 17; and further comprising a sleeve inserted in said casing and receiving said pack of ligature wires, said push rod being guided in said sleeve to press onto the top of said pack.

19. The combination according to claim 10, wherein said access means through which said wires are removable from said casing includes a centering sleeve for guiding a tool for grasping the ligature wire, said centering sleeve being mounted in said casing at a transfer point for the wire being removed from said casing.

* * * * *